US005700465A

United States Patent [19]
Tao et al.

[11] Patent Number: 5,700,465
[45] Date of Patent: Dec. 23, 1997

[54] BOVINE SERUM AND BOVINE IGG AS PREVENTIVES AND THERAPEUTIVES FOR BOVINE MASTITIS

[75] Inventors: Weng Tao, Katonah, N.Y.; Martin John Corbett, Mt. Holly, N.J.; Walter C. Pickett, Suffern, N.Y.

[73] Assignee: American Cyanamid Company, Parsippany, N.J.

[21] Appl. No.: 177,833

[22] Filed: Jan. 5, 1994

[51] Int. Cl.$^6$ .................. A61K 39/395; A61K 39/40; C07K 16/00; C07K 16/18
[52] U.S. Cl. .................. 424/130.1; 424/164.1; 424/163.1; 424/165.1; 424/176.1; 530/387.1; 530/389.1; 530/389.5
[58] Field of Search .................. 424/163.1, 164.1, 424/165.1, 169.1, 130.1, 176.1; 530/389.5, 387.1, 389.1

[56] References Cited

U.S. PATENT DOCUMENTS

| | | |
|---|---|---|
| 3,203,865 | 8/1965 | Keebler et al. . |
| 3,917,818 | 11/1975 | Botes et al. . |
| 3,984,539 | 10/1976 | Khouw et al. . |
| 4,096,244 | 6/1978 | Newson et al. . |
| 4,623,541 | 11/1986 | Elliott et al. . |

FOREIGN PATENT DOCUMENTS

| | | |
|---|---|---|
| 49421/74 | 7/1976 | United Kingdom . |
| 48292/76 | 5/1979 | United Kingdom . |
| PCT/US91/08556 | 9/1992 | WIPO . |

OTHER PUBLICATIONS

Fischer, G. W. et al., Reviews of Infect. Dis., 12(4):5483–5491, May–Jun. 1990.
Weisman, L.E. et al., J. Pediat, 115:445–50, 1989.
McGuire, T.C. et al., Immunology, 38:249–256, 1979.
Quiroga, G.H. et al., J. Dairy Science, 76:2913–2924, 1993.
Effect of Immune Complexes from Mastitic Milk on Blocking of Fc Receptors and Phagocytosis, Infection and Immunity, Feb. 1985. pp. 484–488.
Biology of Human Immunoglobulin g Fc Receptors, Journal of Leukocyte Biology 49:511–524 (1991).
Reactive Oxygen Product Formation after Fcγ receptor–mediated neutrophil activation by monomeric mouse IgG2a: implications for the generationof first does effects after OKT3 treatment, Eur. J. Immunol. 1993. 23:977–980.
Polymorphonuclear Leukocyte Function Triggered Through the High Affinity Fc Receptor for Monomeric IgG$^1$, The Journal of Immunology, vol. 139. 534–538, No. 2 Jul. 15, 1987.
Interactions of monomeric IgG bearing covalently bound C3b with polymorphonuclear leucocytes, Immunology 1987, 15–20.
Role of the Oxidative Metabolic Burst inth Antibody–dependent Cellular Cytotoxicity Mediated by Neutrophil Polymorphonuclears, Exp. Hematol, Nov. 1982, vol. 10, No. 10, pp. 859–866.

Bovine IgG1, but not IgG2, binds to human B cells and inhibits antibody secretion, Immunology, 1990, 69 361–366.
Bovine Milk IgG, but not serum IgG, inhibits pokeweed Mitogen–Induced Antibody Secretion by Human Peripheral Blood Mononuclear Cells, Joournal of Clinical Immunology, Vo. 7, No. 1, 1987.
Phagocytosis of target particles bearing C3b–IgG colvalent complexes by human monocytes and polmorphonuclear leucocytes, Immunology, 1987, 62 45–51.
Stimulation of human neutrophil chemiluminescence by soluble immune complexes and antibodies to neutrophils, vol. 98 No. 2.
Differential Stimulation by oxygen–free–radical–altered immunoglobulin G of the production of superoxide and nitrogen peroxide by human polymorphonuclear leucocytes, Clinical Science (1991) 80, 385–391.
Human IgG Fc receptor heterogeneity: molecular aspects and clinical implications, Immunolgy Today, vol. 14, No. 5 1993, 215–221.
Signal transduction by Fc receptors: the Fc&Ri case, Immunology today, Vo. 14 No. 5 1993 pp. 222–226.
Immunoglobulins, Inflammation: Basic Principles and Clinical Correlates, SecondEdition, 1992, pp. 11–31.
Structure, Signaling, and Function of FcγR, Inflammation: Basic Principles and Clinical Correlates, Second Edition, 1992, pp. 497–510.
Bovine Neutrophils Recruited by Endotoxin to a Teat Cistern Continuously Produce Oxygen Radicals and Show Increased Phagocytosis and Extracellular Chemiluminescence, Inflammation, Vo. 16, No. 2, 1992, pp. 117–113.
Surface receptors for immunoglobulin on bovine polymorphonuclear neutrophils and macrophages, Research in Veterinary Science, 1980, 29, 128–130.
Phagocytic Activity of Milk Leukocytes During Chronic Straphylococcal Mastitis, J Dairy Sci, 1988, 71:780–787.
Antibydo–dependent cellular cytotoxicity of *Trypanosoma theileri*mediated by purified bovine isotypes and subisotypes, Parasite Immunology, 1985, 7, 179–189.
Activation of complement by and IgG molecule without a genetic hinge, Letters to Nature, vol. 363, 1993, p. 628.
The Potentiation by TNF–α and PMA of Fc Receptor–mediated phagocytosis in neutrophils is independent of reactive oxygen metabolites produced by nadph oxidase and of protein kinase C, Biochemical and Biophysical Research Cummunications, vol. 193, No. 3, 1993, p. 919.
Complement, Immunoglobulins and Fc Receptors II (4600–4605); Wednesday AM, A1731.
Immunological Aspects of Mammary Involution, J Dairy Sci, 1989, 72:1665–1678.

(List continued on next page.)

*Primary Examiner*—Susan A. Loring
*Attorney, Agent, or Firm*—Hamilton, Brook, Smith & Reynolds, P.C.

[57] ABSTRACT

Immunoglobulin G-2 (IgG2), e. g. bovine IgG2, and its reaction with neutrophils can be used to enhance the neutrophil's functional status in host animal defense against bacterial infections.

7 Claims, 7 Drawing Sheets

OTHER PUBLICATIONS

Quantitavie Studies of Fc Receptors on Bovine Leukemic Blood Lymphcytes; Characterization by Binding of Homologous IgG1 and IgG2, Veterinary Immunology and Immunopathology, 13 (1986) 111–120.

Preparation of Polymorphonuclear Leucocytes–Plasma Membranes which Show Fc Receptor Activity, J. Biochem, 92, 1891–1900 (1982).

The Expression of Fc Receptors on Guinea–pig Peritoneal Macrophages and Neutrophils, Immunology, 1983, 48 647.

The Phagocytic Activity of Polymorphonuclear Leucocytes Isolated formNormal Uterus and that with Experimentally Induce Inflammation in Cows, J. Vet. Med. A 37, 506–512 (1990).

The Pagocytic Activity of Neutrophil Granulocytes Isolated from Blood, Mammary Gland and Uterus of Cows, Polski Archiwum Weterynaryine 30, 3–4, 1990.

A role for IgM inthe in vitro opsonisationof *Staphylococcus aureus*and *Escherichia coli* by bovine polymorphonuclear leucocytes, Research in Veterinary Science 1982, 33, 47–53.

The Capacity of Various Types of Immunoglobulin for Intravenous Use to Interact with Fc Receptors of Human Monocytes and Macrophages, Blut, 1986, 53: 321–332.

Receptors for Aggregated (a) IgG on bovine neutrophils (PMN) are down regulated by activation of potein kinase C (PKC) and are sensitive to phosphatidyl inositol specific phospholipase C (PIPLC, Annual Meeting Abstracts, 1992 48.

Comparison of C3b binding to bovine peripheral blood and mammary gland neutrophils (PMN), Annual Meeting Abstracts, 1992, 48

Protection Against Gram–Negative Bactermia in Neutrophenic Mice with Recombinant Granulocyte–Macrophage ColonyStimulating Factor, Cytokine, Vo.2 No. 4 (Jul. 1990) 287–293.

Interferons Augment Expression of Fc Receptors for Both Monomeric and Heat–aggregated IgG on bovine macrophages, Res 1987 42(4): 353–354, J. Leukocyte Biology.

Effect of Polymeric IgG on Human Monocyte Functions, Int. Arch, Allergy Appl. Immunol, 1987, 158–167).

Characterization of Surface Receptors on Bovine Leukocytes, Int. Arch Allergy Appl Immunol, 1978, 56, pp. 289–300.

The Isolation, Long–term Cultivationand Characterization of Bovine, peripheral blood monocytes, Immunobiol. Program, Vet. Med. Res. Inst, *807–814), 1980.

Mediators of Inflammation (1682–1687), Sunday AM Abstracts.

Immunoglobulins, Lysozyme and Lactoferrin in the Teat and Udder of the Dry Cow during Endotoxin–Induced Inflammation, J. Vet. Med. B 39, 165–174, (1992).

Phagocytosis and Intracellular Killing of *Staphylococcus aureus*by Bovine Blood Polymorphonuclear Leukocytes after Migration, J. Vet. Med. B 36, 154–156 (1989).

Bactericidal Activity of Standard Bovine Serum Against Coliform Bacteria Isolated from Udders and the Environment of Dairy Cows, Am. J. Vet. Res., vol. 38, No. 12, pp. 2019–2022 (1977).

Signal Transduction Events and FcγR Engagement in HumanNeutrophils Stimulated iwth immune Complexes, The Fournal of Immunology, Vo. 146, 735–741, No. 2, (1991).

Phagocytosis of Serum–Resistant and Serum–Sensitive Coliform Bacterial (Klebsiella) By Bovine Neutrophils from Blood and Mastitic Milk, Am. J. Vet. Res, vol. 39, No. 3, pp. 425–427, (1978).

β–Glucuronidase Release from Human Monocyts Induced with Aggregated Immunoglobulins of Different Classes, Cellular Immunology 98, 57–67 (1986).

Assoication of Immunoglobulin G Fc Receptor II with Src–like Protein–tyrosine Kinase Fgr in neutrophils, Proc. Natl. Acad. Sci. USA, vol. 90, p.6305, (1993) 1st page only.

Distribution of Immunoglobulin–Bearing Leukocytes in Bovine Mammary Tissue Infected Chronically with *Staphylococcus aureus*, J. Vet. Med. B 37, 473–476 (1990).

Inhibition of lacteal leukocyte phagocytosis by colostrum, nonlactating secretion, and mastitis milk, Am J. Vet. Res. vol. 47, No. 9, 1940–1945 (1986).

Fc Receptor Expression, Concanavalin–A capping, and enzyme content of bovine neonatal neutrophils: a comparative study with adult cattle, Journal of Leukocyte Biology, vol. 51, pp. 264–269 (1992).

Comparison of Bovine IgG1, IgG2 andIgM for Ability to Promote Killing of Mycoplasma Bovis by Bovine Alveolar Macrophages and Neutrophils, Veterinary Immunology and Immunopathology, 6 (1984) 321–326.

Cytotooxic and Blocking Effect of Bovine Colostrum, J. Vet. Med. B 35, 96–104 (1988).

The Interaction of Ruminant IgG with Rececptor Type II for IgG on Human Phagocytes, Immunology 1989, 66, 143–148.

Polymorphonuclear Neutrophil Leukocyte Function in Clinical Bovine Patients and in Cows with or without *Staphylococcus aureus*Mastitis, Veterinary Reseach Communications, 16 (1992) 107–115.

The Binding of HumanImmunoglobulin G1 Monomer and Small, Covalently Cross–Linked Polymers of Immunoglobulin G1 to Human Peripheral Blood Monocytes and Polymorphonuclear Leukocytes, J. Clin. Inest, vol. 69, pp. 1–8, (1982).

Mechanisms of Cell–Mediated Cytotoxicity II 5304–5309, Wednesday PM.

Synergism Between Antibody and Neutrophils in the Ruminant Mammary Gland, Veterinary Immunology and Immunopathology, 17 (1987) 389–400.

BOVINE SERUM AND BOVINE IGG AS PREVENTIVES AND THERAPEUTIVES FOR BOVINE MASTITIS

FIELD OF INVENTION

The present invention relates to bovine IgG2 its reaction with bovine neutrophils to enhance host defense against bacterial infections.

BACKGROUND OF THE INVENTION

Immunoglobulin (Ig) plays an important role in host immunity and inflammation. The F(ab')$_2$ portion of the immunoglobulin mediates antigen binding, and is responsible for the specific immune response, whereas the Fc portion of the immunoglobulin determines the effector function of the antibody, such as complement fixation, placenta traversal and Fc receptor binding. Most of our knowledge about effector function of immunoglobulin and Fc receptors are derived from studies in human or murine systems. Most functional studies are performed using physically or chemically aggregated immunoglobulin to mimic immune complex formed under physiological and pathophysiological conditions.

The release of reactive oxygen species (superoxide) represents one of the major systems through which polymorphonuclear leukocytes (neutrophils) kill invading organisms. Immunoglobulin, in immune complex form, or aggregated form has been reported to induce superoxide production in human neutrophils. Fc receptor aggregation is important for human neutrophil activation.

There are separate receptors for aggregated IgG, IgG1 and IgG2 on bovine neutrophils. However, the interaction of immunoglobulin with the corresponding receptor, specificity and the biological consequences of these interactions are not clear. Pathogen-specific ovine IgG2 will stimulate ovine mammary derived neutrophils, providing that ewes are appropriately immunized with live pathogens. Bovine IgG2 also enhances the killing of *Mycoplasma bovis* by bovine alveolar macrophages and neutrophils. The current invention is focused on the effector functions of monomeric bovine immunoglobulin and superoxide production in bovine neutrophils induced by bovine IgG.

SUMMARY OF THE INVENTION

The present invention relates to the use of Immunoglobulin G-2 (IgG2) and its reaction with neutrophils to enhance the neutrophil's functional status in host animal defense against bacterial infections.

More particularly, the present invention relates to the use of bovine IgG2 to enhance the function of bovine neutrophils in host animal defense against specific bacterial infections.

One aspect of the invention relates to a method for prevention of bacterial infections whereby neutrophil functional status is enhanced by host inoculation with IgG2 immunoglobulin.

Another aspect of the invention relates to treating infections caused by bacteria in animal hosts using IgG2 immunoglobulin.

In yet another embodiment, the bovine IgG2 can be administrated in combination with antibiotics as therapeutic agents. Bovine IgG2 enhances neutrophil bacterial killing capability through increased phagocytosis and superoxide production, therefore reducing the existing bacterial levels in the host.

Bacterial-specific bovine IgG2 can be produced and isolated. The bacterial-specific bovine IgG2 can serve both as an effective opsonic material and as an effective neutrophil function enhancer, thereby having a dual therapeutic effect for a specific infectious disease.

DETAILED DESCRIPTION OF THE INVENTION

The bovine IgG2 of the present invention is prepared by isolating IgG2 from serum samples derived from an appropriate host animal, as for example a cow, pig, goat, sheep or rabbit, with a species IgG isotype specific column. Methods for production of IgG2 have been previously described and are herein incorporated by reference (Schmerr, et al., J. Chromatography 326, 225–233). Bacterial-specific IgG2 are produced by immunizing the appropriate host animal, with a specific bacterial derived antigen and boosted with additional immunizations. Serum from non-immunized host and immunized host is collected and isolated.

Bovine plasma (heat inactivated) induces a dose dependent increase in superoxide production in bovine neutrophils. The minimum effective concentration of plasma is a 1:1,000,000 dilution. Plasma concentrations between 1:1,000,000–1:10,000 dilution, induce a dose dependent increase in superoxide production. Higher concentrations of plasma result in an inhibition of superoxide production. Similar profile of response is observed with serum without the heat inactivation procedure.

The effect of unfractionated bovine plasma protein G column "Flow Through Fraction", protein G "unbound Fraction" and eluted "IgG Fraction" on superoxide production shows that IgG induces a dose dependent increase in superoxide production. Significant induction can be seen at 1:10,000 dilution and maximum induction at 1:100 dilution. Compared to IgG, unfractionated plasma induces a much lower level of superoxide production and maximum induction can be seen at 1:1,000 dilution; higher concentration (1:100) does not induce superoxide production. Both "Flow Through Fraction" and "Unbound Fraction" have no effect on superoxide production in bovine neutrophils.

Monomeric bovine IgG induces a dose dependent increase in superoxide production in bovine neutrophils. Significant effect is observed at about 1 mg/ml while maximum effect is achieved at about 100 mg/ml of IgG as presented in FIG. 3. Higher concentration results in a decline of the induction.

Figure 4:
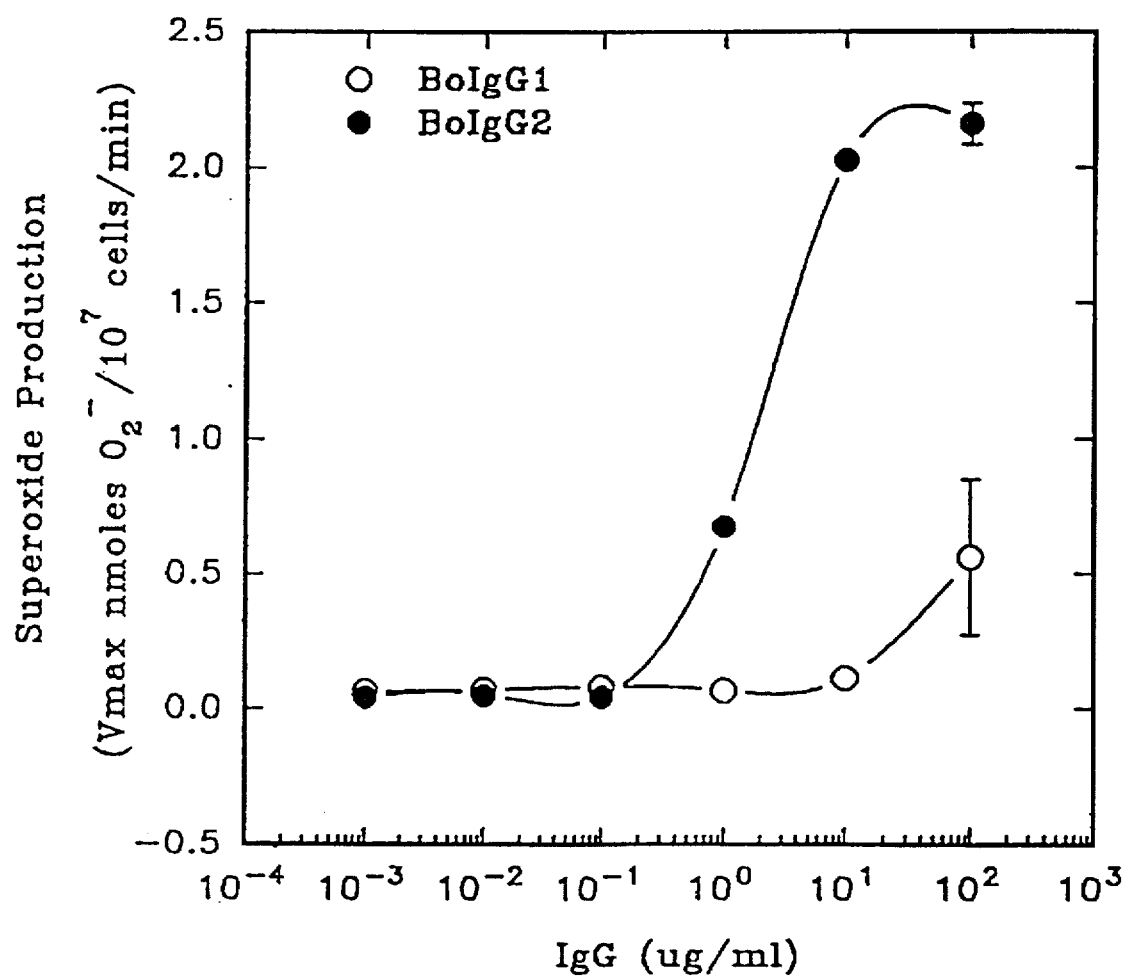
FIG. 4 shows the effect of monomeric bovine IgG1 and bovine IgG2 on superoxide production in bovine neutrophils. Bovine neutrophils ($1\times10^6$ cells/ml) are incubated with different concentrations of bovine IgG1 or bovine IgG2 at 37° C., superoxide production is monitored from time 0 to 30 min. The results are expressed as Vmax nmoles $O_2^-/10^7$ cells/min The data represent the Mean±SEM of three separate experiments.

Monomeric bovine IgG2 induces a dose dependent superoxide production in bovine neutrophils. Significant induction can be seen at 1 mg/ml of IgG2 with maximum induction being achieved at 100 µg/ml. Bovine IgG1 was not effective except at very high concentration (100 µg/ml). The results are presented in FIG. 4.

Figure 5:
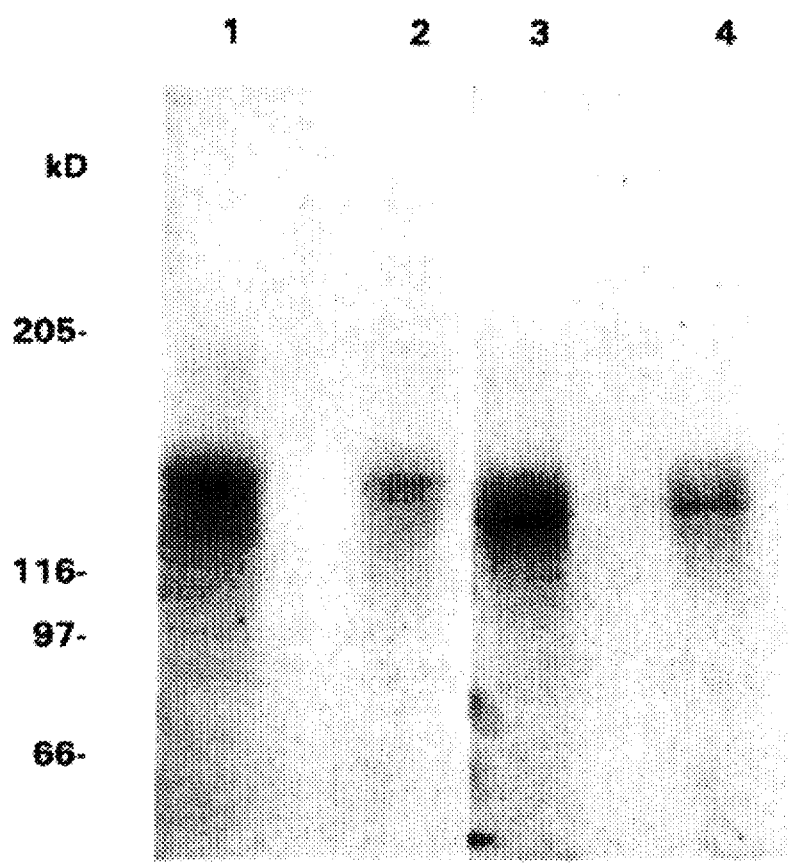
FIG. 5 shows the SDS-PAGE analysis of monomeric bovine IgG1 and IgG2 preparation. IgG2 (lanes 1 and 2) and IgG1 (lanes 3 and 4) are either untreated (lanes 1 and 3) or centrifuged at 100,000×g (lanes 2 and 4). Supernatants containing 30 µg IgG are analyzed on Coomassie stained non-reduced 2–10% linear gradient SDS-PAGE.

Bovine IgG1 and IgG2 are analyzed on non-reducing 2–10% gradient SDS-PAGE gels to determine the presence or absence of IgG dimers or oligomers (FIG. 5). IgG1 and IgG2 both have approximate mol. wt. of 160 kDa with no detectable dimers or oligomers identified by Coomassie blue staining. Centrifugation at 100,000×g collects IgG monomer species in the supernatant. Centrifugation supernatants of IgG1 and IgG2 (lanes 2 and 4) appears identical to the unfractionated samples (lanes 1 and 3) indicating that this commercial source of bovine IgG contains no detectable dimers or oligomers.

Bovine IgG induces a dose dependent increase in superoxide production. In contrast, both IgG F(ab)$_2$ and Fc are not effective. The results are presented in FIG. 6.

Figure 7:
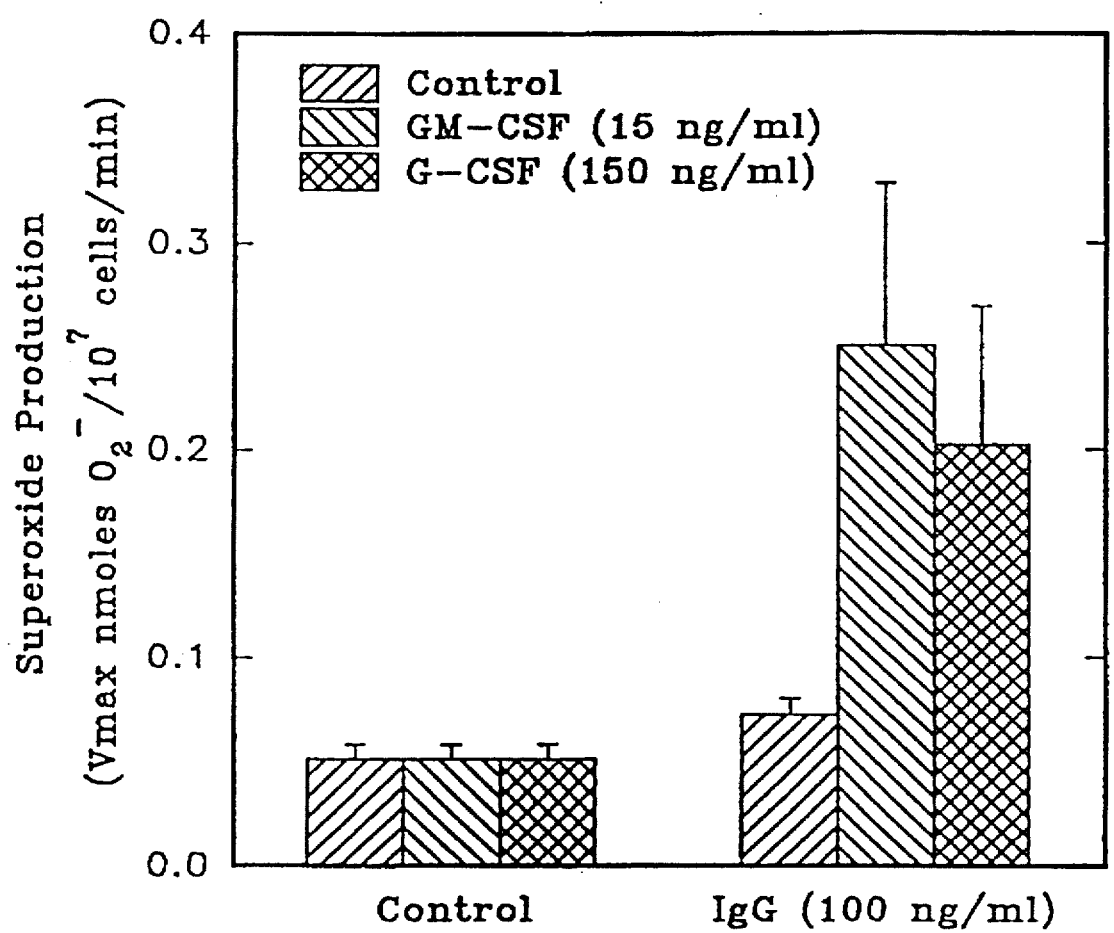
FIG. 7 shows the priming effect of r-BoGM-CSF and r-BoG-CSF on superoxide production in bovine neutrophils induced by bovine IgG. Bovine neutrophils are incubated with either r-BoGM-CSF or r-BoG-CSF (concentrations as indicated) at 37° C. for 45 min. before the addition of bovine IgG. Superoxide production is monitored from time 0 to 30 min after IgG stimulation. The results are expressed as Vmax nmoles $O_2^-/10^7$ cells/min. The data represent the mean±SEM of three separated experiments.

The priming effects of r-BoGM-CSF and r-BoG-CSF on superoxide production induced by bovine IgG are examined. Bovine neutrophils are incubated with either r-BoGM-CSF or r-BoG-CSF at 37° C. for 45 minutes before the addition of bovine IgG. Pretreatment of bovine neutrophils with r-BoGM-CSF ($1\times10^{-9}$M) or r-BoG-CSF ($1\times10^{-8}$M) significantly enhances superoxide production induced by suboptimal concentration of bovine IgG (100 ng/ml). The results are presented in FIG. 7.

The prophylactic effect of bovine IgG on *staph. aureus* mastitis are examined in an in vivo challenge model. Six Holstein-Fresian dairy cattle are used for this study. All the mammary glands have been negative for *Staph. aureus* for at least 21 days prior to treatments. Bovine mammary glands are randomized for three separate treatment groups. Seven glands (group 1) received PBS, six glands (group 2) received 10 mg IgG/gland, and seven glands (group 3) received 100 mg/gland. All infusions were made into the teat cistern of a milked out mammary gland after the PM milking, and followed by *Staph. aureus* challenge (Newbould 305, 300 CFU) at time 0. AM milk samples were collected from all glands. Microbiology (*Staph. aureus* counts) was performed daily for 14 consecutive days. Signs of toxicosis were monitored through out 14 days. Among the seven glands receiving PBS prior to *Staph. aureus* challenge, all the glands were infected with *Staph. aureus*, therefore PBS gave 0% protection. Among the six glands receiving 10 mg IgG/gland, two glands were free of infection. Therefore, 10 mg IgG gave 33.3% protection. Among the seven glands receiving 100 mg/gland, three glands were free of infection indicated 43% protection with 100 mg IgG. These data indicate the utility of IgG as a prophylactic agent for contagious bovine mastitis.

Figure 1:
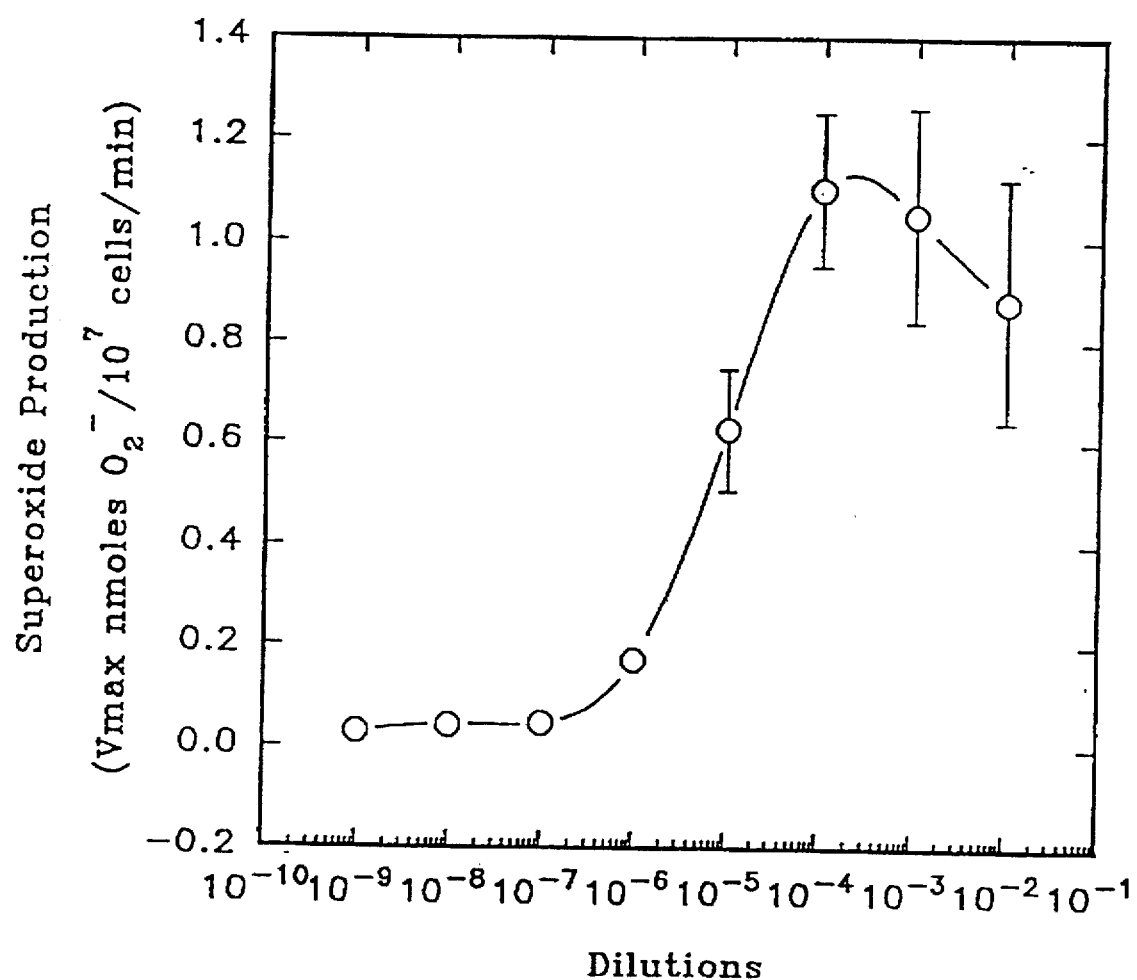
FIG. 1 shows the effect of bovine plasma dilutions on superoxide production in bovine neutrophils. Bovine neutrophils ($1\times10^6$ cells/ml) are stimulated with different concentrations of heat inactivated (56° C., 30 min.) bovine plasma in HBSS at 37° C., and superoxide production is monitored from time 0 to 30 min. after stimulation. The results are expressed as Vmax nmoles $O_2^-/10^7$ cells/min. The data represent the mean±SEM of three separate experiments.
Figure 2:
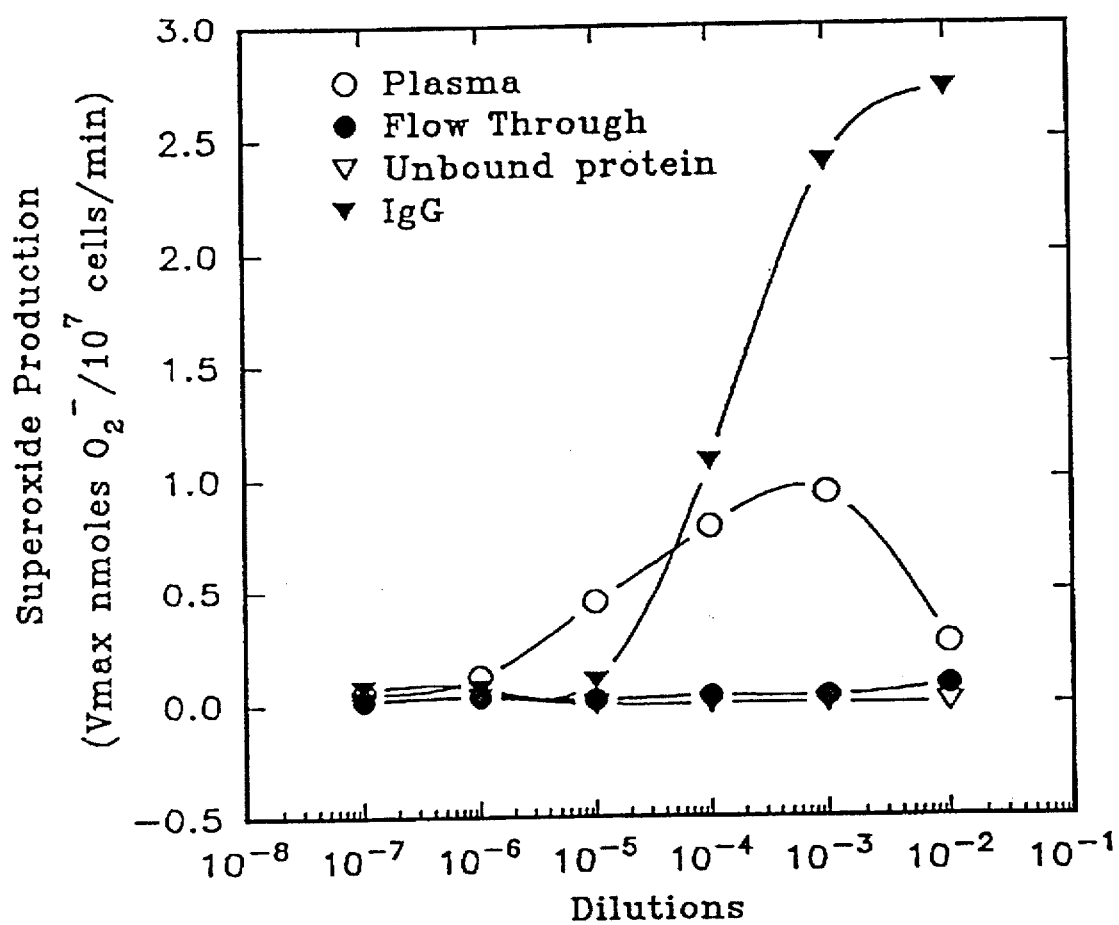
FIG. 2 shows the effect of bovine plasma and plasma fractions on superoxide production in bovine neutrophils. Bovine neutrophils ($1\times10^6$ cells/ml) are incubated with different concentrations of bovine plasma, plasma "Flow Through" and "Unbound Protein" fractions and IgG (as indicated) at 37° C. Superoxide production is monitored from time 0 to 30 min. The results are expressed as Vmax nmoles $O_2^-/10^7$ cells/min. The data represent one of three such experiments.

Bovine plasma contain factors which can stimulate bovine neutrophils for an enhanced superoxide production. Bovine IgG, purified from plasma induced superoxide production in bovine neutrophils. Both "Flow Through" and "Unbound Protein" fractions were not effective (FIG. 2), showing that bovine IgG is one of the major components of serum stimulatory factor. When similar IgG concentrations were tested, the purified IgG induced a much stronger response than that of plasma IgG (FIG. 2). This finding suggests that in the normal physiological state, neutrophils in the circulation are protected from these stimulating serum factors by inhibitory factors.

Figure 3:
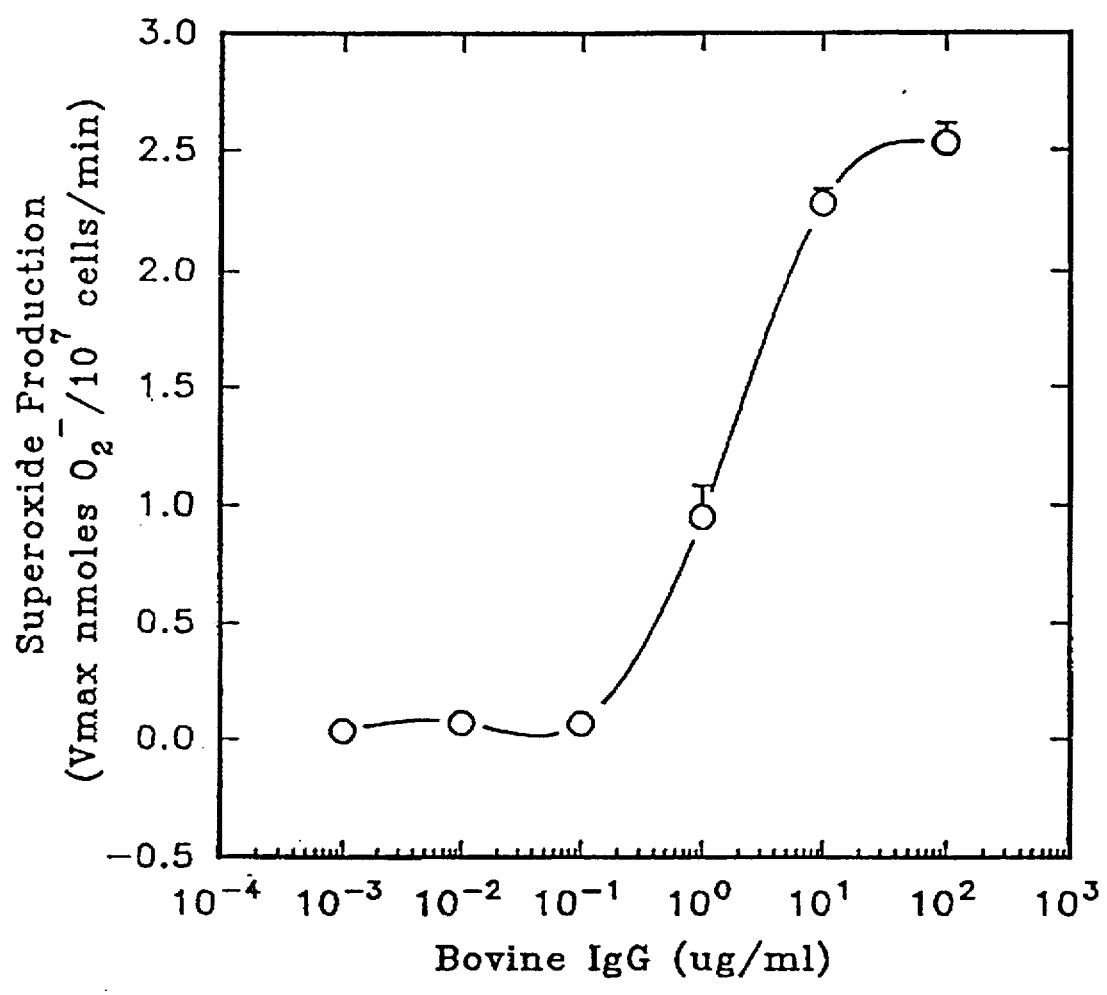
FIG. 3 shows the effect of monomeric bovine IgG on superoxide production in bovine neutrophils. Bovine neutrophils ($1\times10^6$ cells/ml) are incubated with different concentrations of bovine IgG at 37° C. Superoxide production is monitored from time 0 to 30 min. The results are expressed as Vmax nmoles $O_2^-/10^7$ cells/min. The data represent the mean±SEM of three separate experiments.

Monomeric bovine IgG, in the absence of crosslinkage, induces a dose dependent increase in superoxide production (FIG. 3). This observation is different from that in the human system in which only aggregated IgG or an immune complex can induce superoxide production, while monomeric IgG is not effective. Binding of monomeric human IgG to human neutrophils is barely detectable, although high affinity Fc receptor for monomeric human IgG can be induced by IFN-γ. However, monomeric mouse IgG2a, an antibody specific for human T cell receptors, has been reported to induce respiratory burst in human neutrophils (Zlabinger, et al., Eur. J. Immunol. 23, 977–980). The current invention demonstrates that in the bovine system monomeric IgG can stimulate homologous neutrophils with high affinity. This observation provides evidence that there are major differences between bovine neutrophils and human neutrophils.

When subclasses of bovine IgG are examined, bovine IgG2 induces superoxide production, and bovine IgG1 is 100–200 fold less effective (FIG. 4), indicating the importance of Fc portion of IgG in neutrophil activation. The functional difference between bovine IgG1 and IgG2 is also observed in inhibition of antibody secretion by human B cells. To examine whether IgG dimers or oligomers are present in the purified IgG1 and IgG2 preparations, prior to use in a bioassay, a sample of IgG1 or IgG2 is centrifuged at 100,000×g to remove dimers or oligomers. The supernatants are then collected and analyzed on a non-reducing linear 3–10% SDS-PAGE gel (FIG. 5). Centrifugation supernatants of IgG1 and IgG2 (FIG. 5, lanes 2 and 4) appear identical to the unfractionated samples (FIG. 5, lanes 1 and 3) indicating that this commercial source of bovine IgG contains no detectable dimers or oligomers. Therefore, monomeric bovine IgG2 is a potent stimulus for bovine neutrophils. Although bovine neutrophils express receptors for both IgG1 and IgG2, IgG2-Fc receptor appears to be the most important in mediating superoxide production.

Bovine colostrum contains high levels of IgG1 compared to IgG2 and neutrophils in the mammary glands are relatively inactive compared to that of blood neutrophils indicating the importance of IgG2 in neutrophil function. In addition, the opsonic activity of normal milk was considerably lower than that of fresh bovine serum. This observation is consistent with an earlier report by Howard, et al., Vet. Immunol. and Immunopathology 6, 321–326, that in a in vitro killing assay by bovine neutrophils, only the IgG2 but not the IgG1 preparation promoted killing by neutrophils. The current invention discloses the result that bovine IgG2 and its receptors play an important role in antimicrobial function of neutrophils in tissue. Bovine IgG2 alone, in the absence of pathogen or crosslinker, is a potent stimulus for bovine neutrophils.

Figure 6:
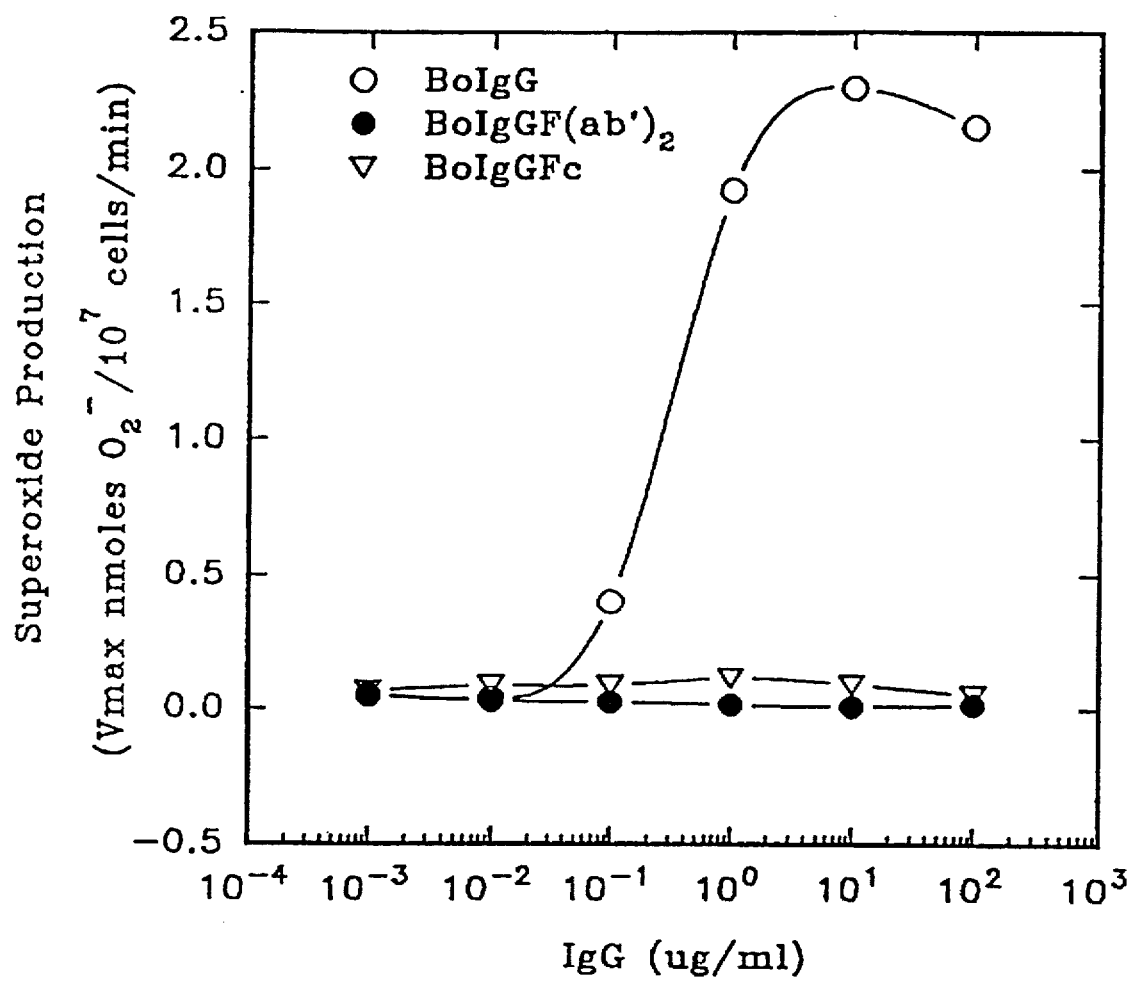
FIG. 6 shows the effect of bovine IgG F(ab')$_2$ and Fc on superoxide production in bovine neutrophils. Bovine neutrophils ($1\times10^6$ cells/ml) are incubated with different concentrations of bovine IgG (control) and bovine IgG F(ab')$_2$ or Fc at 37° C., superoxide production is monitored from time 0 to 30 min. The results are expressed as Vmax nmoles $O_2^-/10^7$ cells/min. The data represent the Mean±SEM of three separate experiments.

Although bovine IgG is a potent stimulus, both IgG F(ab')$_2$ and Fc are not effective in inducing superoxide production (FIG. 6). This observation shows that the integrity of IgG is important for its activity.

Pretreatment of bovine neutrophils with either r-BoGM-CSF or r-BoG-CSF enhances superoxide production induced by bovine IgG (FIG. 6). r-BoGM-CSF primes bovine neutrophils for an enhanced superoxide production induced by platelet-activating factor (PAF) and interleukin-1. However, r-BoG-CSF does not prime PAF induced superoxide production suggesting that bovine IgG induced bovine neutrophil activation can be primed by both r-BoGM-CSF and r-BoG-CSF, and the site of priming is probably at the receptor level.

Pretreatment of bovine mammary glands with bovine IgG at 10 mg/gland or 100 mg/gland protected 33% and 43% glands from infection respectively. These results show the beneficial effect of bovine IgG in host protection.

While the invention has been described in detail, it will be appreciated by those of ordinary skill in the art that modifications can be made to the structure and elements of the invention without departing from the aspect and scope of the invention as a whole.

EXAMPLE 1

Isolation of Peripheral Blood Neutrophils

Bovine blood is collected by jugular venipuncture into acid citrated dextrose. Bovine polymorphonuclear leukocytes (PMNs) are isolated by a method described previously by Heidle et al. (J. Leukoc. Biol. 46, 41–45 (1989)) which is herein incorporated by reference. Briefly, 45 ml whole blood is centrifuged in 50 ml conical polypropylene tubes for 20 min. at room temperature at 1000×g. Plasma and buffy coat are aspirated and the remaining cells are diluted to the original volume with phosphate buffered saline (PBS) and centrifuged at 1000×g for 15 min. PBS and the remaining buffy coat are aspirated and the erythrocytes (RBC) are lysed by hypotonic shock using 20 ml ice cold phosphate-buffered distilled $H_2O$ (1.82 g Na/Phosphate monobasic/liter of distilled $H_2O$, pH 7.2) and gently rocking for 45 second. Immediately, 10 ml of ice cold PBS with 2.7% NaCl is added to restore isotonicity. Cells are centrifuged at 1000×g at 4° C. for 10 min. A second lysis is performed if substantial RBCs remains. Cells are washed twice and quantitated by a hemocytometer. Cell viability is determined by trypan blue exclusion. Cells are then resuspended in Hanks' balanced salt solution (HBSS) at $5\times10^6$ cells/ml, and stored on ice until use.

EXAMPLE 2

Purification of IgG from Bovine Serum

Bovine IgG is purified from bovine plasma with Monoclonal antibody (MAb) Trap G column. Prior to collection of purified antibody fractions, 60 ml of neutralizing buffer is added to collection tubes per ml of fraction. A sample of plasma (2.5 ml) is centrifuged at 10,000×g for 10 minutes and passed through a 0.22 µm filter. The sample is diluted 1:4 with binding buffer. Binding buffer is then added to the Protein G Sepharose column and allowed to drain.

The prepared sample (10 ml) is then added to the frit and allowed to absorb into the gel. The flow through fraction is collected and the above procedure repeated twice. The final flow through fraction is collected as "Flow Through" (FT fraction, 10 ml). Binding buffer (10 ml) is then passed through the column to elude the unbound materials which is collected as "unbound" (UB fraction, 10 ml). The bound IgG is eluted by filling the column with elution buffer (10 ml). The antibody is than collected in the prepared collection tubes (IgG fraction, 10 ml). The protein concentration in the IgG fraction is determined by opticaldensity 280 (O.D.$_{280}$) with a spectrophotometer.

EXAMPLE 3

Preparation of Monomeric Bovine IgG

Before use in studies requiring IgG1 and IgG2 monomer, purified bovine IgG1 and IgG2 is centrifuged at 100,000×g for 30 min to eliminate aggregates which might have formed during storage. A SDS-PAGE analysis of the above sample is carried out to ensure the quality of the preparation. IgG samples are resolved on a non-reducing linear 3–10% SDS-PAGE gel using an acrylamide:bisacrylamide ratio of 37.5:1. Gels are stained with Coomassie blue. This gel system has the capacity to resolve high molecular weight proteins up to 900 kd.

EXAMPLE 4

Superoxide Anion Assay

Superoxide production is determined at 37° C. using a 96-well microtiter plate assay. The release of $O_2^-$ was measured as the superoxide dismutase inhibitable reduction of cytochrome C at 550 nm. The rate of $O_2^-$ production was monitored from time 0 to 30 min. and the end point $O_2^-$ production was measured 30 min. after stimulation. The reaction mixture contained in a total volume of 250 µl including 50 µl of cells at $5\times10^6$ cell/ml ($2.5\times10^5$ cells/well), 200 µl of cytochrome C in HBSS at 219 µM (final concentration: 175 µM) and indicated stimuli (volume not more than 5 µl) in the absence or presence of superoxide dismutase (SOD, 5 µl/180 units/well). The results were reported either as rate of $O_2^-$ production (Vmax nM $O_2^-/10^7$ cells/min) or end point $O_2^-$ production (total nM $O_2^-/10^7$ cells). The rate and amount of superoxide production was calculated using the molecular extinction coefficient for cytochrome C (24, 25). Briefly, the rate of superoxide production was calculated from the rate of cytochrome C reduction minus the rate of cytochrome C reduction in the presence of superoxide dismutase (SOD, 180 units/well) multiplied by 0.5952 according to the following equation:

$$Vmax=(mOD_{abs}-mOD_{sod})\times 0.5952=\text{nmoles } O_2^-/10^7 \text{ cells/min.}$$

The end point total superoxide production was calculated from the absorbance of total cytochrome C reduction minus the total cytochrome C reduction in the presence of SOD multiplied by 595.2.

Total $O_2^- = (OD - OD_{sod}) \times 595.2 =$ nmoles $O_2^-/10^7$ cells.

EXAMPLE 5

Cows and In Vivo Challenge Model

The prophylactic effect of bovine IgG on *staph. aureus* mastitis is examined in an in vivo challenge model. Six Holstein-Fresian dairy cattle were used for this study. All the mammary glands have been negative for *Staph. aureus* for at least 21 days prior to treatments. Bovine mammary glands are randomized for three separate treatment groups. Seven glands (group 1) receive PBS, six glands (group 2) receive 10 mg IgG/gland, and seven glands (group 3) receive 100 mg/gland. All infusions are made into the teat cistern of a milked out mammary gland after the PM milking, and followed by *Staph. aureus* challenge (Newbould 305, 300 CFU) at time 0. AM milk samples are collected from all glands. Microbiology (*Staph. aureus* counts) is performed daily for two weeks. Signs of toxicosis are monitored through out two weeks. The criterion for an infected gland is detection of *Staph. aureus* in the milk sample at least for two consecutive days after challenge. The criterion for a protected gland is negative detection of *Staph. aureus* throughout the 14 day period after *Staph. aureus* challenge. Table 1 below summarizes the results of this experiment.

TABLE 1

PROPHYLACTIC EFFECT OF IgG FOR *S aureus* MASTITIS

| TREATMENT | % PROTECTION |
| --- | --- |
| PBS Control | 0/7 = 0% |
| 10 mg IgG | 2/6 = 33.3% |
| 100 mg IgG | 3/7 = 43% |

REFERENCES

1. Gallin, J., Goldstein, I. M., Snyderman, R., eds. (1992) Inflammation, Basic Principles and Clinical Correlates. Raven Press, New York.
2. Unkeless, J. C., Scigliano, E., Freedman, V. H. (1988) Structure and function of human and murine receptors for IgG. Annu. Rev. Immunol. 6, 251–281.
3. Anderson, C. L. (1989) Human IgG Fc receptors. Clin. Immunol. Immunopathol. 53, S63–S71.
4. Odin, J. A., Painter, C. J., Unkeless, J. C. (1990) Fc gamma receptors: a diverse and multifunctional gene family. In: Cochrane, C. G., Gimbrone, M. A. Jr, eds. Receptors of inflammatory cells: structure-function relationship. Cellular mechanisms of inflammation. Vol.1 Orlando, Fla.: Academic Press, 1–33.
5. Burton, D. R. (1985) immunoglobulin G: Functional sites. Mol. Immunol. 22, 161.
6. Lachmann, P. J., Hughes-Jones, N. C. (1984) Initiation of complement activation. Springer Semin Immunopathol. 7, 143.
7. van de Winkel, J. G. J., Anderson, C. L. (1991) Biology of human immunoglobulin G Fc receptors. J. Leukoc. Biol. 49, 511.
8. Steplewski, Z., Sun, L. K., Shearman, C. W., Ghrayeb, J., Daddona, P., Koprowski, H. (1988) Biological activity of human-mouse IgG1, IgG2, IgG3, and IgG4 chimeric monoclonal antibodies with antitumour activity. Proc. Natl. Acad. Sci (USA) 85, 4852.
9. Unkeless, J. C., Boros, P., Fein, M. (1992) In: Inflammation, Basic Principles and Clinical Correlates. Raven Press, New York. PP. 497.
10. Jefferis, R., Pound, J. D. (1992) In: Inflammation, Basic Principles and Clinical Correlates. Raven Press, New York. pp.11.
11. Kleinveld, H. A., Sluiter, W., Boonman, A. M. C., Swaak, A. J. G., Hack, C. E., Koster, J. F. (1991) Differential stimulation by oxygen-free-radical-altered immunoglobulin G of the production of superoxide and hydrogen peroxide by human polymorphonuclear leukocytes. Clinical Science 80, 385–391.
12. Mandell, G. L. (1974) Bactericidal activity of aerobic and anaerobic polymorphonuclear neutrophils. Infect. Immun. 9, 337–341.
13. Vel WAC, Namavar, F., Verweij, A., Marian, J. J., Pubben, A. N. B., MacLaren, D. M. (1984) Killing capacity of human polymorphonuclear leukocytes in aerobic and anaerobic conditions. J. Med. Microbiol. 18, 173–180.
14. Worku, M., Paape, M. J., Marquardt, W. W. (1992) Interferon-gamma upregulated Fc-gamma receptors (Fc-gamma-R) for monomeric IgG on bovine neutrophils (PMN) by de-novo RNA transcription and protein synthesis. FASEB J. 6, (5). A1731.
15. Worku, M., Paape, M. J., Marquardt, W. W. (1992) Receptors for aggregated (a) IgG on bovine neutrophils (PMN) are down regulated by activation of protein kinase C (PKC) and are sensitive to phosphatidyl inositol specific phospholipase C (PIPLC). J. Leukoc. Biol. 3 (supplement). 48.
16. Watson, D. L. (1976) The effect of cytophillic IgG2 on phagocytosis by ovine polymorphnuclear leukocytes. Immunology 31, 159.
17. Howard, C. J. (1984) Comparison of bovine IgG1, IgG2 and IgM for ability to promote killing of *Mycoplasma bovis* by bovine alveolar macrophages and neutrophils. Vet. Immunol. and Immunopathology 6, 321–326.
18. Schmerr, M. J. F., Goodwin, K. R., Lehmkuhl, H. D. and Cutlip, R. C. (1985) Preparation of sheep and cattle immunoglobulins with antibody activity by high-performance liquid chromatography. J. Chromatography 326, 225–233.
19. Lambin, P., Rochu, D., Fine, J. M. (1976) A new method for determination of molecular weight of proteins by electrophoresis across a sodium dodecyl sulfate (SDS) - polyacrylamide gradient gel. Analytical Biochemistry 74, 567–575.
20. Kurlander, R. J., Batker, J. (1982) The binding of human immunoglobulin G1 monomer and small, covalently cross-linked polymers of immunoglobulin G1 to human peripheral blood monocytes and polymorphonuclear leukocytes. J. Clin. Invest. 69, 1–8.
21. Newbould, F. H. S. and Neave, F. K. (1965) The response of the bovine mammary gland to an infusion of Staphylococci. J. Dairy Res. 32, 163.
22. Starkebaum, G., Stevens, D. L., Henry, C., Gavin, S. E. (1981) Stimulation of human neutrophil chemiluminescence by soluble immune complexes and antibodies to neutrophils. J. Lab. Clin. Med. 98, (2) 280–291.
23. Malbran, A., Frank, M. M., Fries, L. F. (1987) Interaction of monomeric IgG bearing covalently bound C3b with polymorphonuclear leucocytes. Immunology 61, 15–20.
24. Shen, L., Guyre, P. M., Fanger, M. W. (1987) Polymophonuclear leukocyte function triggered through the high affinity Fc receptor for monomeric IgG. J. Immunol. 139, 534–538.

25. Zlabinger, G. J., Rosenkranz, A. R., Schmaldienst, S., Stuhlmeier, K., Bohmig, G., Stockl, J., Pohanka, E., Kovarik, J. (1993) Reactive oxygen product formation after Fcγ receptor-mediated neutrophil activation by monomeric mouse IgG2a: implications for the generation of first dose effects after OKT3 treatment. Eur. J. Immunol. 23, 977–980.

26. Gray, G. D., Knight, K. A., Nelson, R. D., Herron, M. J. (1982) Chemotactic requirements of bovine leukocytes. Am. J. Vet. Res. 43, 757–759.

27. Rausch, P. G., Moore, T. G. (1975) Granule enzymes of polymorphonuclear neutrophils: a phylogenetic comparison. Blood 46, 913–919.

28. Gennaro, R., Schneider, C., DeNiicola, G., Cian, F., Romeo, D. (1978) Biochemical properties of bovine granulocytes. Proc. Soc. Exp. Med. 157, 342–347.

29. Kulczcki, JR., A., Nash, G. S., Bertovich, M. J., Burack, H. D., Macdermott, R. P. Bovine milk IgG, but not serum IgG, inhibits pokeweed mitogen-induced antibody secretion by human peripheral blood mononuclear cells. J. Clin. Immunol. 7, (1) 37–45.

30. Nash, G. S., Macdermott, R. P., Schloemann, S., Bertovich, M. J., O'Neal, J., Porter, L., Kulczycki, A. (1990) Bovine IgG1, but not IgG2, binds to human B cells and inhibits antibody secretion. Immunology 69, 361–366.

31. Targowski, S. P., Niemialtowski, M. (1986) inhibition of lacteal leukocyte phagocytosis by colostrum, nonlactating secretion, and mastitic milk. Am. J. Vet. Res. 47, 1940–1945.

32. Zwahlen, R. D., Wyder-Walther, M., Roth, D. R. (1992) Fc receptor expression, concanavalin A capping, and enzyme content of bovine neonatal neutrophils: a comparative study with adult cattle. L. Leuko. Biol. 51, 264–269.

33. Targowski, S. P., Niemialtowski, M. (1988) Cytotoxic and blocking effect of bovine colostrum. J. Vet. Med. B 35, 96–104.

34. Watson, D. L. (1987) Synergism between antibody and neutrophils in the ruminant mammary gland. Veterinary Immunology and Immunopathology 17, 389–400.

35. Jain, N. C., Lasmanis, J. (1977) phagocytosis of serum-resistant and serum-sensitive coliform bacteria (Klebslella) by bovine neutrophils from blood and mastitic milk. Am. J. Vet. Res. 39, 425–429.

36. Burton, D. R., Jefferis, R., Partridge, L. J., Woof, J. M. (1988) Molecular recognition of antibody (IgG) by cellular Fc receptor (FcR1). Mol. Immunol. 25, 1175–1181.

37. Ducan, A. R., Woof, J. M., Partridge, L. J., Burton, D. R. Winter, G. (1988) Localization of the binding site for the human high-affinity Fc receptor on IgG. Nature 332, 563–564.

38. Tao, W., Dougherty, D., Johnston, P., Pickett, W. (1993) Recombinant bovine GM-CSF primes superoxide production but not degranulation induced by recombinant bovine interleukin-1β in bovine neutrophils. J. Leuko. Biol. 53, 679–684.

39. Heidel, J. R., Taylor, S. M., Laegreid, W. W., Silflow, R. M., Liggitt, H. D., Leid, R. W. (1989) Characterization of arachidonic acid metabolism, superoxide production, and bacterial killing in bovine circulating neutrophils and elicited alveolar neutrophils. J. Leukoc. Biol. 46, 41–45.

40. Pick, E., Mizel, D. (1981) Rapid microassays for the measurement of superoxide and hydrogen peroxide production by macrophages in culture using automatic enzyme immunoassay reader. J. Immunol. Methods 46, 211–226.

41. Mayo, L. A. and Curnutte, J. T. (1990) Kinetic microplate assay for superoxide production by neutrophils and other phagocytic cells. Methods Enzymol. 186, 567–575.

What we claim is:

1. A method of treating infection caused by *Staphylococcus aureus* in bovine animal host cells comprising administering an appropriate dosage of monomeric bovine IgG2 immunoglobulin obtained from non-immunized animals to a bovine animal host whereby the IgG2 immunoglobulin reacts with IgG2-Fc receptors and stimulates neutrophil function in the host animal cell.

2. A method of preventing infection caused by *Staphylococcus aureus* in bovine animal host cells comprising administering an appropriate dosage of monomeric bovine IgG2 immunoglobulin obtained from non-immunized animals to a bovine animal host whereby the IgG2 immunoglobulin reacts with IgG2-Fc receptors and stimulates neutrophil function in the host animal cell.

3. The method of claim 1 or 2 wherein the appropriate dosage is between 10–100 mg.

4. The method of claim 1 or 2 wherein the dosage is administered by a route selected from the group consisting of intravenous injection, intramuscular injection, mammary gland infusion, and slow release formulation.

5. The method of claim 1 or 2 wherein the infection is bovine mastitis.

6. The method of claim 5 wherein the bovine mastitis is contagious.

7. The method of claim 5 wherein the bovine mastitis is environmental.

* * * * *